United States Patent [19]

Schubert

[11] Patent Number: 4,475,902

[45] Date of Patent: Oct. 9, 1984

[54] DEVICE FOR INTRODUCING MEDICAL INSTRUMENTS INTO A BODY

[76] Inventor: Werner Schubert, Dohne 32, 4330 Mülheim/Ruhr, Fed. Rep. of Germany

[21] Appl. No.: 361,117

[22] Filed: Mar. 23, 1982

[30] Foreign Application Priority Data

Mar. 24, 1981 [DE] Fed. Rep. of Germany ....... 3111497

[51] Int. Cl.³ .............................................. A61M 25/00
[52] U.S. Cl. ...................................... 604/95; 604/256
[58] Field of Search ................ 604/95, 247, 256, 264, 604/275, 279, 280–283

[56] References Cited

U.S. PATENT DOCUMENTS

| 1,115,908 | 11/1914 | Dees | 604/95 |
|---|---|---|---|
| 2,356,659 | 8/1944 | Aguiar | 604/95 |
| 3,071,137 | 1/1963 | Niebel et al. | 604/95 |
| 3,470,876 | 10/1969 | Barchilon | 604/95 |
| 3,605,725 | 9/1971 | Bentov | 604/95 X |
| 3,726,283 | 4/1973 | Dye et al. | 604/247 X |
| 3,895,637 | 7/1975 | Choy | 604/95 |
| 4,248,234 | 2/1981 | Assenza et al. | 604/256 X |
| 4,403,985 | 9/1983 | Boretos | 604/95 X |

FOREIGN PATENT DOCUMENTS

| 331872 | 10/1903 | France | 604/275 |
| 2267800 | 11/1975 | France | 604/95 |

Primary Examiner—Dalton L. Truluck

[57] ABSTRACT

A device for introducing medical instruments into hollow organs, canals, or vessels of a human or animal body, has a tip which is provided with an indentation. At least a first nozzle, aimed rearwardly with respect to the tip and connected to an inner chamber of the tip, extends through the wall of the indentation and is connected to a source of pressurized fluid. The pressurized fluid escaping from the nozzle exerts a force on the tip to advance it into the body, and a instrument coupled to the nozzle tip is thereby transported through the body.

7 Claims, 5 Drawing Figures

DEVICE FOR INTRODUCING MEDICAL INSTRUMENTS INTO A BODY

BACKGROUND OF THE INVENTION

In medicine, instruments such as catheters, probes endoscopes, etc., are introduced into the human or animal body for diagnosis or therapy as well as for the withdrawal of rtissue samples. For example, in the treatment of humans instruments may be introduced into the urethra, the ureter, the cervical canal, the esophagus, the stomach, the small intestine and especially the large intestine, which exhibits cancerous degeneracies or their precursors with particular frequency. Instruments are also frequently introduced also into veins or arteries in order to reach the heart chambers, lung arteries, or the like. Since the necessary instruments are introduced into the body from the outside, injuries to the hollow organs, intestines, vessels, and tissue for example, perforations result.

To achieve a more gentle introduction of a proctoscope for large intestine diagnosis or therapy, attempts have previously been made to attach this instrument to the end of an inner section of an inverted tube. The space between the two tube sections is connected to a source of pressurized fluid, and the inner section of the tube is pushed into the large intestine by the pressure prevailing between the two tube sections. The fluid pressure causes the inner tube section to invert as it carries the proctoscope and at the end of the insertion procedure the proctoscope comes into contact with the intestinal wall. However, the inner tube section in this case rolls out on the intestinal mucous membrane and produces frictional artifacts, which may be the reason why this device has not become important in practice, particularly since the changes caused by the introduction of the device make a diagnostic evaluation of the mucous membrane, etc., difficult.

SUMMARY OF THE INVENTION

One object of this invention consists of making possible the introduction of medical instruments into the body in a gentle manner while avoiding the drawbacks mentioned above.

Another object of the invention consists of providing a device for introducing medical instruments into body openings which is of simple construction and is therefore inexpensive to manufacture.

An additional object of the invention consists of providing a device for introducing medical instruments into body openings which is simple to handle.

In accordance with this invention, a device for introducing medical instruments into hollow organs, canals, or vessels of a human or animal body, includes a nozzle tip having at least one peripheral indentation which defines a plane perpendicular to the longitudinal axis of the tip. One or more nozzle orifices, connected to an inner chamber of the nozzle tip, extend through the wall of the indentation. The inner chamber is connected to a source of a pressurized fluid via a pressure tube which is fastened at one end to the nozzle tip. The orifice or orifices are oriented so that fluid discharged therefrom will produce force having a component which advances the tip into the body. An instrument is coupled to the nozzle tip and is thus transported through the body.

A gentle transport of the particular instrument through the body is thus achieved in a simple manner, without adversely affecting the tissue and without the possibility of perforations.

Other purposes, benefits, and designs of the invention will become apparent in the following description.

DETAILED DESCRIPTION OF THE PREFERRED EMBODIMENTS

Figure 1:
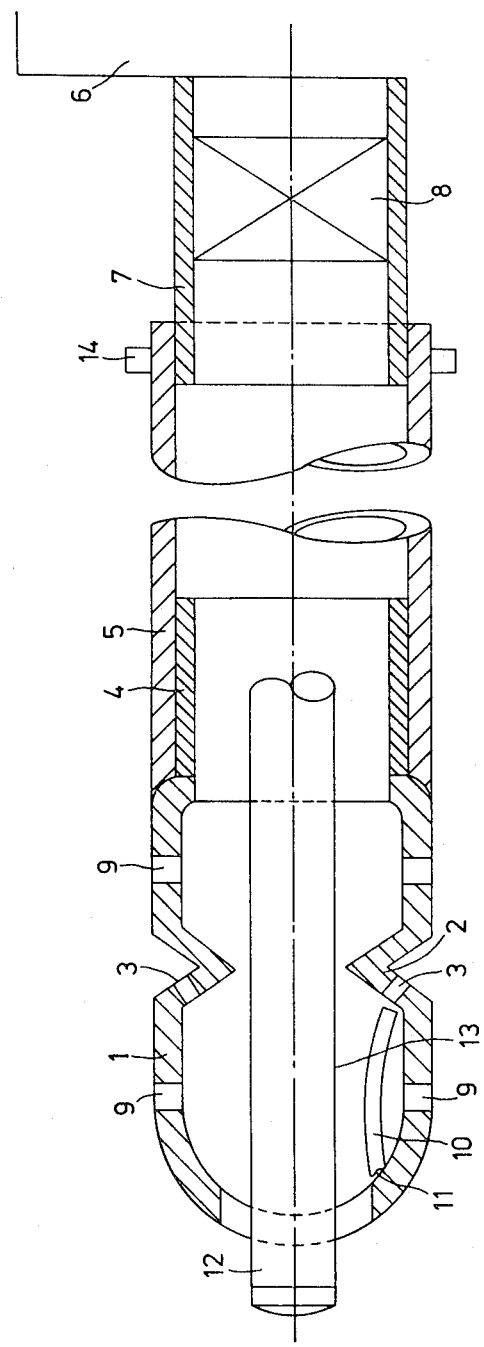
FIG. 1 is an enlarged cross-sectional schematic side elevation view of a device pursuant to a first embodiment of the invention with an instrument extended therefrom after insertion.

The device illustrated in FIG. 1 includes a nozzle tip 1 having a hemispherical forward or leading end. Tip 1 is provided with a peripheral indentation 2 located a distance from its leading end. The indentation 2 has a V shape in the FIG. 1 embodiment. The forwardly disposed wall of the V-shaped indentation 2 is provided with a number of nozzles 3 which have their axes oriented diagonally backwards relative to the direction of advance of the nozzle tip 1. The rear end 4 of the nozzle tip 1, designed as a connecting tube, is received in a pressure tube 5. Tube 5, in turn, is connected to a pressure tank 6 through a connecting tube 7.

The nozzle tip 1 can be formed of metal or of a plastic, which can optionally also be extensible and flexible, but must have an adequate pressure-resistant capacity.

For rinsing, lubricating and/or expanding the opening into which the instrument is being inserted, the tip 1 may also be provided with orifices 9 which are directed radially outwardly and which may be arranged as a wreath in one or more planes oriented perpendicularly with respect the longitudinal axis of the nozzle tip 1.

Pressurized fluid delivered from the pressure tank 6 through pressure tube 5 into the nozzle tip 1 is discharged through the nozzles 3 to produce a force which urges the nozzle tip in the forward direction through the hollow organ, canal, or vessel of the body. The pressurized fluid will be chosen in accordance with the intended application. Thus, a pressurized liquid can be preheated to body temperature, it can be sterilized, and it can be a liquid compatible with the body, such as a physiological saline solution, or the like.

The pressure tank 6 is appropriately equipped with a safely valve and can have a heating device to heat the pressurized fluid to body temperature (neither illustrated).

The nozzle tip 1 illustrated in FIG. 1 also has an opening in its hemispherically shaped end which may be selectively opened and closed by a movable flap on lid 10. A medical instrument 12, such as an endoscope, is received within the nozzle tip 1. When tip 1 reaches desired position in the body, the lid 10, which is hinged at 11 to the nozzle tip 1, opens, and the instrument 12 is pushed out through the opening. The opening of the lid 10 can be accomplished, for example, by a pull cord (not illustrated) running through the pressure tube 5. Lid 10 may, if necessary, or desirable, be biased to the closed position by a spring, not shown.

The method of operation of the device of FIG. 1 is as follows:

By subjecting the nozzle tip 1 to pressurized fluid from the pressure tank 6 through the pressure tube 5, the nozzle tip 1 is moved forward through the large intestine, for example, by the force produced by the liquid jets escaping from the backward-pointing nozzles 3. At the same time, the intestine wall is slightly spread apart by the pressurized fluid discharged through the radially directed openings 9. Accordingly, the nozzle tip 1 easily moves forward through the intestine. When the nozzle tip 1 has reached the desired position in the intestine, the supply of pressurized fluid is shut off and the tip drains, so that the lid 10 opens or may be opened into the position illustrated in FIG. 1. The instrument 12 is then pushed forward through the opening previously covered by the lid 10 until it extends out of the nozzle tip 1. The necessary examinations and treatments can then be undertaken and, for example the entire large intestine can be examined by withdrawing the nozzle tip 1.

Figure 2:
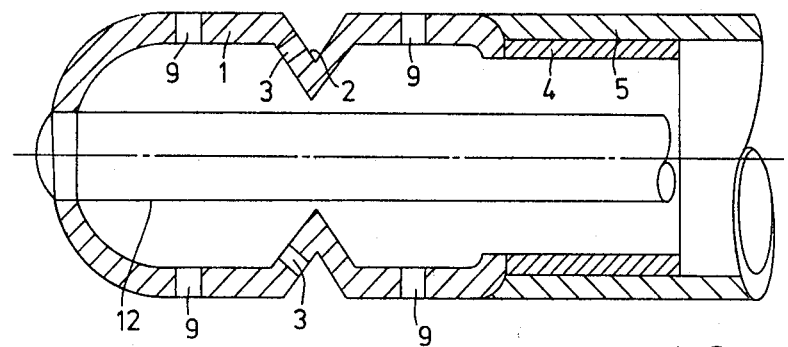
FIG. 2 is a view similar to FIG. 1 showing a second embodiment of the invention having an instrument rigidly mounted therein.

In the embodiment of FIG. 2, the instrument 12 is rigidly installed in the nozzle tip 1 in an orifice at the front end of the nozzle tip 1. However, the instrument 12 can also be coupled in another manner to the nozzle tip 1. For example, it can be set on the front end of the nozzle tip 1, can surround the nozzle tip 1 or can be fastened to an eyelet of the nozzle tip. The instruments can also be moved forward along the pressure tube 5 to the nozzle tip 1, for example, by means of a movable race 14 (FIG. 1).

Figure 3:
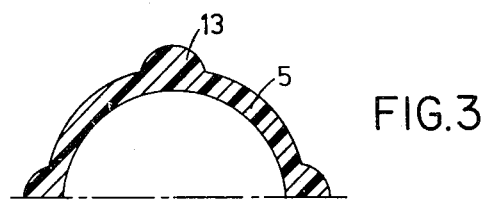
FIG. 3 is a partial cross-sectional view, taken transversely with respect to FIGS. 1 and 2, of a pressure tube for use in the practice of the present invention.

To facilitate the discharge of pressurized fluid, from the body cavity or passage, the pressure tube may be provided with soft longitudinal ribs 13, as shown in FIG. 3.

Figure 4:
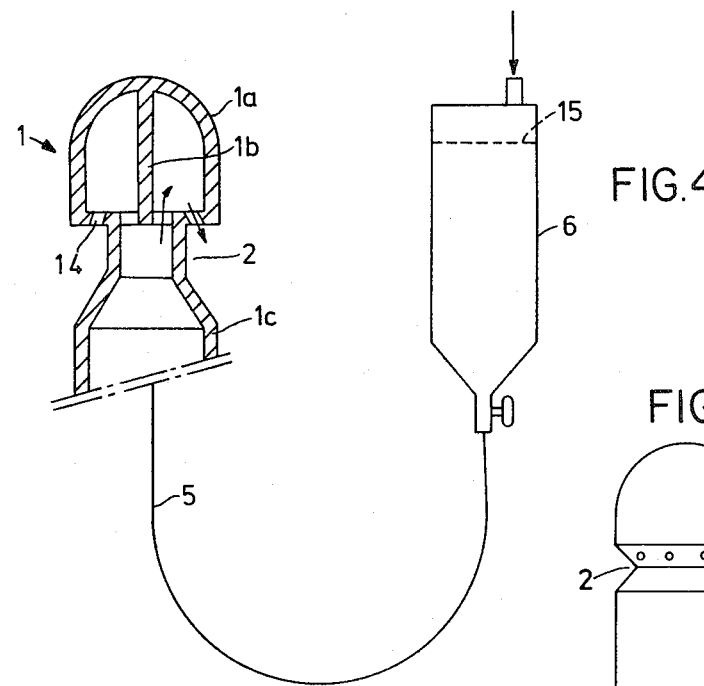
FIG. 4 is a partial cross-sectional schematic side elevation view of a further embodiment of the invention.

In the embodiment of FIG. 4, the nozzle tip 1 itself serves as the instrument for flushing or rinsing a body cavity and for this purpose it is provided with an annular nozzle 14 in the area of the encircling indentation 2. Annular opening 14 is oriented diagonally rearwardly and the pressurized liquid discharged therethrough provides both for the necessary advancing force and for the production of an annular rinsing jet. This jet can be adjusted to the appropriate gentleness by the choice of the width of the annular slit 14. In the FIG. 4 embodiment the forward section 1a of the nozzle tip 1 is connected to and supported from the rear section 1c of the nozzle tip 1 by a central bridge 1b.

As shown in FIG. 4, the pressure tube 5 may be connected to the lower end of a pressure tank 6, for example a plastic bottle, in which a pressurized medium, for example a gas such as air or the like, can be introduced from above by means of a pump or the like to compress, either directly or via a piston, the liquid 15 in the pressure tank 6.

Figure 5:
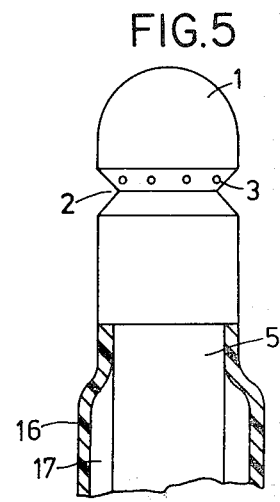
FIG. 5 is a partial cross-sectional schematic side elevation view of a portion of yet another embodiment of the present invention.

The embodiment illustrated in FIG. 5 may be used as an instrument for dilating vessel constrictions. For this purpose, the pressure tube 5 is surrounded by another tube 16. The space 17 between the pressure tube 5 and tube 16 is connected to a source of pressurized fluid (not shown). The tube 16 is designed to be dilatable over part or all of its length, so that it can be enlarged in diameter by introducing the pressurized fluid into the intermediate space 17. The front end of the tube 16, for example, can be cemented or welded to the pressure tube.

The device pursuant to the invention is not limited to the embodiments illustrated and described, but is quite generally suitable for the direct or indirect transport of medical instruments, and can be used, for example, for the flushing of gallstones, bladder stones, or kidney stones, or can carry an abrasion instrument with which tissue samples can be withdrawn, for example from the cervical canal.

I claim:

1. Apparatus for use in the delivery of a medical instrument into an opening in a living organism, said apparatus being intended for insertion into the opening and comprising:

a tip portion, said tip portion having a cylindrical body portion and a generally hemispherically-shaped forward end which extends from said body portion, said body portion having a longitudinal axis and an inner diameter which is greater than the outer diameter of the medical instrument to be delivered therethrough, said tip portion being provided with a circumferential recess in the exterior surface of the side wall of said body portion, said recess being displaced from said tip portion forward end, said tip portion forward end being provided with an opening commensurate in size and shape with the cross-section of the medical instrument to be delivered, the medical instrument being mounted in said opening in said tip portion forward end;

an internal chamber, said chamber being in part defined by said tip portion;

a plurality of nozzles for establishing fluid communication between said recess in the exterior surface of said body portion and said internal chamber, said nozzles having axes which are angularly oriented with respect to said longitudinal axis whereby fluid discharged therefrom will be directed outwardly and rearwardly with respect to said tip portion to produce a reactive force component which urges said apparatus in the direction of further insertion of said tip portion, the discharge ends of said nozzles being recessed with respect to the exterior surface of said tip portion body portion and defining a plane which is generally transverse to said longitudinal axis;

tubular support means for said tip portion, said support means defining an extension of said internal chamber and coupling said internal chamber to a source of pressurized fluid; and means for causing dialation of the opening into which the apparatus is inserted.

2. Apparatus for use in the delivery of a medical instrument into an opening in a living organism, said apparatus being intended for insertion into the opening and comprising:

a tip portion, said tip portion having a cylindrical body portion and a generally hemispherically-shaped forward end extending from said body portion, said body portion having a longitudinal axis and an inner diameter which is greater than the outer diameter of the medical instrument to be delivered therethrough, said tip portion being provided with a circumferential recess in the exterior surface of the side wall of said body portion, said recess being displaced from said tip portion forward end, said tip portion forward end being provided with an opening commensurate in size and shape with the cross section of the medical instrument to be delivered;

flap means for selectively opening and closing said opening in said tip portion forward end, the medical instrument being extendable through said opening when said flap means is in the open position;

an internal chamber, said chamber being in part defined by said tip portion;

a plurality of nozzles for establishing fluid communication between said recess in the exterior surface of said body portion and said internal chamber, said nozzles having axes which are angularly oriented with respect to said longitudinal axis whereby fluid discharged therefrom will be directed outwardly and rearwardly with respect to said tip portion to produce a reactive force component which urges said apparatus in the direction of further insertion of said tip portion, the discharge ends of said nozzles being recessed with respect to the exterior surface of said tip portion body portion and defining a plane which is generally transverse to said longitudinal axis;

tubular support means for said tip portion, said support means defining an extension of said internal chamber and coupling said internal chamber to a source of pressurized fluid; and means for causing dialation of the opening into which the apparatus is inserted.

3. Apparatus for use in the delivery of a medical instrument into an opening in a living organism, said apparatus being intended for insertion into the opening and comprising:

a tip portion, said tip portion having a cylindrical body portion and a generally hemispherically-shaped forward end extending from said body portion, said body portion having a longitudinal axis and an inner diameter which is greater than the outer diameter of the medical instrument to be delivered therethrough, said tip portion being provided with a circumferential recess in the exterior surface of the side wall of said body portion, said circumferential recess being displaced from said tip portion forward end, said tip portion forward end being provided with an opening commensurate in size and shape with the cross section of the medical instrument to be delivered;

an internal chamber, said chamber being in part defined by said tip portion;

a plurality of nozzles for establishing fluid communication between said recess in the exterior surface of said body portion and said internal chamber, said nozzles having axes which are angularly oriented with respect to said longitudinal axis whereby fluid discharged therefrom will be directed outwardly and rearwardly with respect to said tip portion to produce a reactive force component which urges said apparatus in the direction of further insertion of said tip portion, the discharge ends of said nozzles being recessed with respect to the exterior surface of said tip portion body portion and defining a plane which is generally transverse to said longitudinal axis;

support means for said tip portion, said support means comprising a first elongated tube which defines an extension of said internal chamber, said support means coupling said internal chamber to a source of pressurized fluid;

a second tube surrounding said first elongated tube, said second tube having at least one flexible portion; and means connecting the region between said first and second tubes to a source of pressurized fluid whereby said flexible portion of said second tube may be expanded to dialate the opening into which said apparatus has been inserted.

4. The apparatus of claim 1 or 2 wherein said support means comprises:

an elongated tube, said tube having a plurality of longitudinal ribs extending from its outer circumference.

5. The apparatus of claim 1 or 2 wherein said means for dialating comprises:

nozzle means, said nozzle means having an axis which is generally transversely oriented with respect to said longitudinal axis, said nozzle means establishing fluid communication between said internal chamber and the exterior surface of the side wall of said tip portion body portion whereby fluid discharged through said nozzle means will exert an expanding force on the walls of the opening into which said apparatus has been inserted.

6. The apparatus of claims 1, 2 or 3 further comprising:

tank means, said tank means being intended to receive a working liquid;

means coupling said support means to a first end of said tank means whereby said working liquid may be delivered to said internal chamber; and means for delivering a pressurized gas to said tank means to cause pressurization of the liquid therein.

7. The apparatus of claim 5 further comprising:

tank means, said tank means being intended to receive a working liquid;

means coupling said support means to a first end of said tank means whereby said working liquid may be delivered to said internal chamber; and means for delivering a pressurized gas to said tank means to cause pressurization of the liquid therein.

* * * * *